(12) United States Patent
Chin et al.

(10) Patent No.: US 6,734,000 B2
(45) Date of Patent: May 11, 2004

(54) NANOPOROUS SILICON SUPPORT CONTAINING MACROPORES FOR USE AS A BIOREACTOR

(75) Inventors: Vicki I. Chin, La Jolla, CA (US); Sangeeta N. Bhatia, La Jolla, CA (US); Michael J. Sailor, La Jolla, CA (US); Boyce E. Collins, La Jolla, CA (US)

(73) Assignee: Regents of the University of California, Oakland, CA (US)

( * ) Notice: Subject to any disclaimer, the term of this patent is extended or adjusted under 35 U.S.C. 154(b) by 0 days.

(21) Appl. No.: 09/981,691

(22) Filed: Oct. 12, 2001

(65) Prior Publication Data

US 2002/0072116 A1 Jun. 13, 2002

Related U.S. Application Data

(60) Provisional application No. 60/240,652, filed on Oct. 12, 2000.

(51) Int. Cl.$^7$ .................. C12M 11/14; C12M 5/06; C12M 5/08; C12M 1/00; C12P 21/00
(52) U.S. Cl. .................. 435/176; 435/29; 435/71.1; 435/71.2; 435/283.1; 435/395
(58) Field of Search .................. 435/29, 176, 283.1, 435/395, 71.1, 71.2

(56) References Cited

U.S. PATENT DOCUMENTS

| | | | |
|---|---|---|---|
| 5,827,729 | A | 10/1998 | Naughton et al. |
| 6,103,479 | A | 8/2000 | Taylor |
| 6,197,575 | B1 | 3/2001 | Griffith et al. |
| 6,218,182 | B1 | 4/2001 | Naughton et al. |
| 6,228,607 | B1 | 5/2001 | Kersten et al. |

OTHER PUBLICATIONS

Allen, J.W. et al. Advances in Bioartificial Liver Devices, Hepatology. 34:447–455 (2001).
Bellet, D. et al. Controlled Drying: The Key to Better Quality Porous Semiconductors, Advanced Materials, 10:487–490 (1998).
Bhatia, S.N.et al. Controlling cell interactions by micropatterning in co–cultures: Hepatocytes and 3T3 fibroblasts, Journal of Biomedical Materials Research, 34:189–199 (1997).
Bhatia, S.N. et al. Effect of cell–cell interactions in preservation of cellular phenotype: cocultivation of hepatocytes and nonparenchymal cells, The FASEB Journal, 13:1883–1900 (1999).
Bhatia, S.N. et al. Microfabrication of Hepatocyte/Fibroblast Co–cultures: Role of Homotypic Cell Interactions, Biotechnol. Prog., 14:378–387 (1998).
Bhatia, S.N. et al. Tissue Engineering at the Micro–Scale, Biomedical Microdevices 2:2, 131–144 (1999).
Canham, L.T., et al. Derivatized Mesoporous Silicon with Dramatically Improved Stability in Simulated Human Blood Plasma, Advanced Materials, 11:1505–1507 (2000).
Chen, C.C. et al.Size Dependence of Structural Metastability in Semiconductor Nanocrystals, Science, 276:398–401 (1997).
Chin, V. et al. Compatability of Primary Hepatocytes with Oxidized Nanoporous Silicon, Advanced Materials, 13:1877–1880 (2001).
Curtis, A. et al. Topographical control of cells, Biomaterials, 18:1573–1583 (1997).
Curtis A. et al. Nantotechniques and approaches in biotechnology, Trends in Biotechnology, 19:97–101 (2001).
Hodgson, J. Admet–turning chemicals into drugs, Nature Biotechnology, 19:722–726 (2001).
Nagamori, S. et al. Developments in bioartificial liver research: concepts, performance, and applications, Journal of Gastroenterology, 35:493–503 (2000).
Selden, C. et al. What keeps hepatocytes on the straight and narrow? Maintaining differentiated function in the liver, Gut, 44:443–446 (1999).
Steiner, P. et al. Micromachining applications of porous silicon, Thin Solid Films, 255:52–58 (1995).
Stewart, M.P. et al. Chemical and Biological Applications of Porous Silicon Technology, Advaned Materials, 12:859–869 (2000).
Webster, T. J. et al. Enhanced functions of osteoblasts on nanophase ceramics, Biomaterials 21:1803–1810 (2000).

*Primary Examiner*—David M. Naff
(74) *Attorney, Agent, or Firm*—Gordon & Rees LLP

(57) ABSTRACT

A nanoporous silicon support comprising a plurality of macropores is provided to function as a bioreactor for the maintenance of cells in culture in a differentiated state. Each cell or group of cells is grown in an individual macropore and is provided with nutrients such as by perfusion of the nanoporous silicon support with fluid. The macropores may be between 0.2 and 200 microns and be coated with a substance that provides cell adhesion. The support containing cells may be used to used to test compounds for biological activity, metabolism, toxicity, mutagenicity, carcinogenicity or to characterize novel or unknown comounds. The support is sufficiently robust that it may be assembled into larger reactors to simulate organ function or be used for the production of biomolecules.

11 Claims, 4 Drawing Sheets

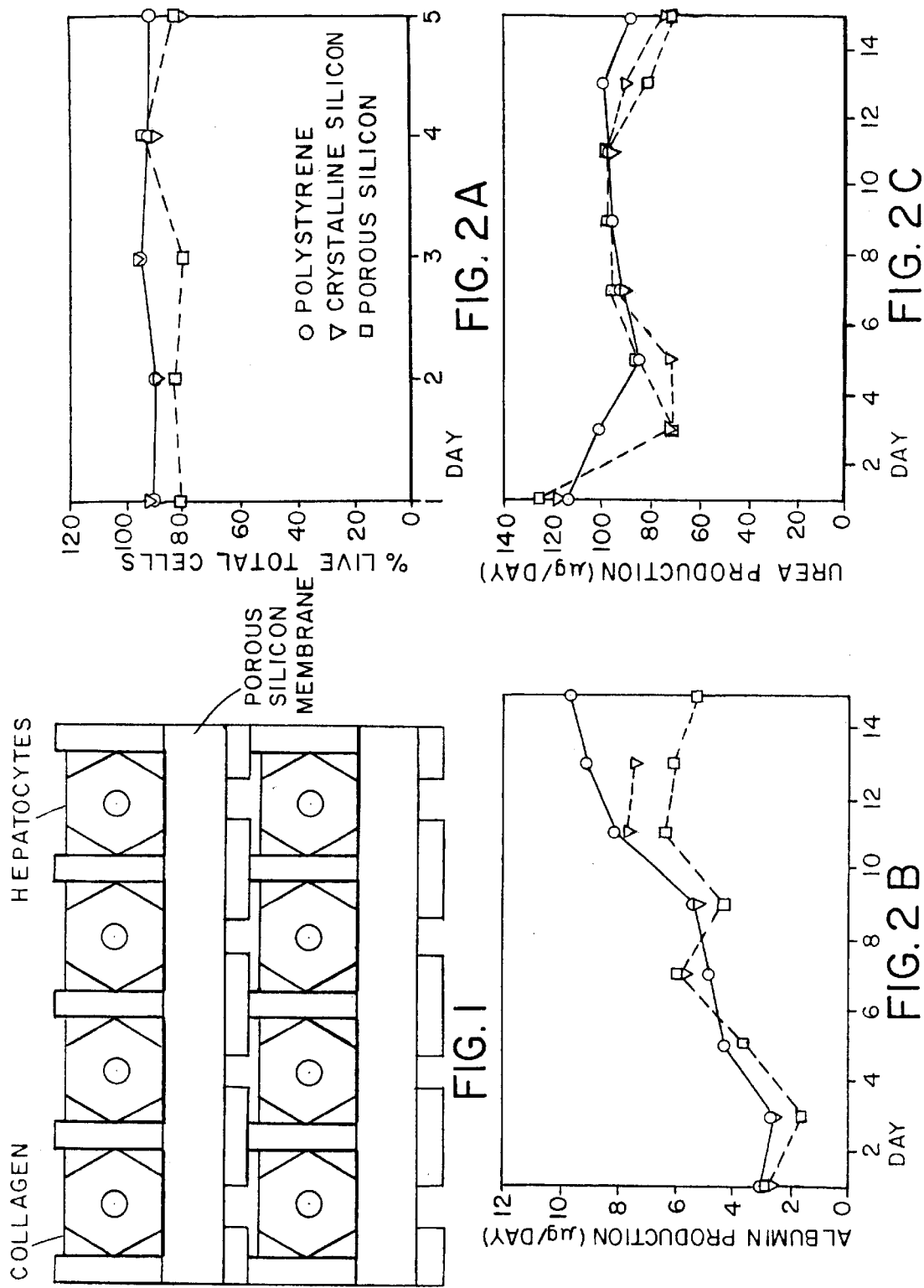

NANOPOROUS SILICON SUPPORT CONTAINING MACROPORES FOR USE AS A BIOREACTOR

CROSS-REFERENCES TO RELATED APPLICATIONS

This application claims the benefit of priority of U.S. provisional application Serial No. 60/240,652 filed Oct. 12, 2000 which is incorporated herein by reference in its entirety.

FIELD OF THE INVENTION

The invention relates to the field of bioreactors. More specifically, it relates to nanoporous silicon bioreactors for the maintenance of cells in culture for use in development and testing of bioactive compounds, protein and metabolite production, and simulated organ function.

BACKGROUND OF THE INVENTION

Silicon has begun to receive increasing attention for use in biomedical applications. In particular crystalline silicon has been utilized as a textured surface to guide cell alignment, to encapsulate cells for implantation, and as an electroactive substrate to stimulate excitable cells. Several properties of silicon have led to its use in these diverse applications: (1) well-described silane chemistries for immobilization of adhesive ligands, (2) wet and dry micromachining capability to form 3-dimensional structures on biologically relevant length scales, and (3) semiconductor properties that allow incorporation of microelectronic elements. In comparison, porous silicon, a nanocrystalline material generated by etching of crystalline silicon in hydrofluoric acid, has been less extensively utilized for biomedical applications. Its open pore structure and large surface area, combined with unique properties such as photo and electroluminescence have provided a platform for sensors for non-biological species (e.g. solvents, gases, and explosives) as well as biological species (DNA, proteins). Indeed, the range of tunable pore sizes (5 to 1200 nm) in porous silicon spans a range of sizes important in biology; a small DNA fragment is on the order of a few tens of nm, proteins are generally in the 100 nm range, and bacteria and cells can be a few microns in diameter.

Previously it has been shown that manipulations of cellular microenvironment by "micropatterning" on inorganic surfaces can alter the behavior of cells in culture (Chen et al, 1997; Bhatia et al, 1999). Methods to alter the support for cell growth to allow for distinct localized cell adhesion involved the manipulation of glass, gold or polymer supports such that cell adhesion molecules were differentially deposited on the support (e.g. U.S. Pat. Nos. 6,004,444; 6,103,479 and 6,133,030; all incorporated herein by reference). A common method involves the use of photoresist, a UV-sensitive polymer. Borisilicate substrates (e.g. coverslips) are coated with photoresist and exposed to light through a mask, creating a photoresist pattern. Patterned substrates are used to control subsequent immobilization of extracellular matrix components (ECM) (e.g. collagen I). The localization of a specific ECM component allows for the adhesion of cells to specific regions of the substrate (e.g. primary hepatocytes adhere to collagen, but not to glass). In some cases, co-cultures of two cell types are achieved by subsequent addition of a second cell type to attach to the periphery. Thus, micropatterned arrays have been used to generate defined co-cultures of hepatocytes and fibroblasts for the study of the maintenance of cell fate and function (Bhatia et al, 1999). Similar arrays have also been used for use in an apparatus for cell based screening. The method may be used for the establishment of any of a number of patterns, including non-uniform arrays (U.S. Pat. No. 6,103,479). However, such a method requires that the cell types of interest have different adhesive properties that are well known. Thus the system is limited to the use of cell types with well defined, and distinct, characteristics.

Some researchers have begun to explore the use of porous silicon as a biodegradable material for the slow release of drugs or essential trace elements to cells or as an in vivo diagnostic[10-12]. Promising findings by Canham et al. have shown hydroxyapatite nucleation on porous silicon in vitro, suggesting that porous silicon, in contrast to crystalline silicon, could be a bioactive surface (Canham, 1995; Canham et al, 1997). Nonetheless, porous silicon has not been extensively characterized as a material for implantation or the formation of hybrid (biological/non-biological) devices in vitro (Rosengren et al, 2000). Studies on the compatibility of this material with mammalian tissues have been performed in immortalized cell lines, that are known to be relatively robust. Cells proliferated in vitro in the presence of silicon and "bulk" metabolic assays revealed no toxicity.

There have recently been a number of papers demonstrating the feasibility of interfacing crystalline silicon and mammalian cells (Mayne et al, 2000; Thomas et al, 1999; Curtis and Wilkinson, 1997). The motivation for such studies includes the fact that silicon is easily manipulated into a variety of structures due to developments in the optoelectronics industry and the production of micro electromechanical (MEMS) devices (Steiner and Lang, 1995; Meyer and Biehl, 1995). Starting with crystalline silicon as a substrate, photolithography and etching techniques allow the facile construction of micron- and submicron-sized structures. Silicon surface chemistries targeting the reactivity of silicon oxide via Si—OH groups and silicon hydride (Si—H) have been well explored allowing a variety of surface modifications (Bhatia et al, 1997; Stewart and Buriak, 2000). Other methods for the modification of silicon included electrodeposition machining, laser ablation, laser drilling, micromachining, lithographic galvanic fabrication (LIGA) and embossing. Furthermore, silicon-based cellular arrays can be easily integrated with other silicon-based components such as sensors, heaters, microfluidics arrays, and the like. Porous silicon has recently received considerable interest in applications as a biomaterial due to its solubility in physiologic environments. The primary dissolution product is silicic acid $[Si(OH)_4]$ a naturally occurring form of silicon that can be processed and excreted by the body. The rate of dissolution can be controlled by chemical derivatization by methods well known to those skilled in the art (Canham et al, 2000).

The use of crystalline silicon chips as a scaffold for the growth of vascularized perfused microtissue and microorgan arrays has been taught by Griffith et al. (U.S. Pat. No. 6,197,575, incorporated herein by reference). The apparatus consists of a micromatrix and a perfusion assembly suitable for seeding and attachment of cells on and throughout the matrix and for morphogenesis of seeded cells into complex, hierarchical tissue or organ structures, wherein the matrix includes channels or vessels through which culture medium, blood, gases or other nutrients or body fluids can be perfused. The functional unit in these micromatricies is the channel containing cells and their exudates (such as extracellular matrix molecules) in the desired morphological structure. The channel refers to a hole with defined dimensions, typically 75–1000 micron across, that goes through a sheet of scaffold material approximately 50–500 micron thick. Each channel is sufficiently large to contain a microscale tissue which is a synthetically formed mass of cells forming a tissue structure or a structure that carries out tissue functions. Griffith suggests that such bioreactors would be ideal to simulate liver. One could seed the micromatricies with endothelial cells, followed by the addition of hepatocytes. Alternatively stem cells may be plated directly onto the scaffold and treated with appropriate growth factors to induce differentiation. Such microtissues can be used in the context of an artificial liver apparatus or in drug toxicity and screening assays.

It would be desirable to develop an artificial liver apparatus, similar to a kidney dialysis apparatus, for hepatic support in individuals waiting for liver transplant. However, the liver is a more complex organ than the kidney which is predominantly responsible for salt balance and filtering of molecules based on size. The liver is responsible for detoxification of xenobiotics and hormones, energy metabolism, production of plasma proteins, and production of bile, rather than the simple filtering, of the blood. Furthermore, the factors that lead to hepatic coma in patients suffering from liver failure have not been identified. Thus sustenance of a patient in liver failure with a device that lacks hepatic cells is unlikely. An artificial liver apparatus would need to contain viable, differentiated hepatic cells in order to function. Furthermore, differentiated hepatic cells must be effectively interfaced with the fluid stream, patient plasma, to allow bidirectional mass transfer of large molecular weight proteins. (Allen et al, 2001)

Development of a simulated liver would also be highly desirable for the testing of drugs, both alone in the process of drug development, and to better understand drug interactions (Hodgson, 2001). Initial drug testing is typically performed on cells in culture to facilitate high throughput screening. However, compounds ingested by a patient must have desirable ADMET (absorption, distribution, metabolism, elimination and toxicity) properties in order to be successful as a drug. Such tests can be performed in animals, however there are a number of drawbacks including expense, variation between species, and growing disfavor of the use of animals in research by the general public. As the liver is the initial site of drug metabolism of orally ingested compounds, a number of methods have been developed to simulate the liver in a laboratory setting. These include the use of isolated liver enzymes (e.g. CYP34A and CYP2D6) to assay for conversion or inactivation of drugs. Such a system does not take into consideration that enzymes in the liver do not exist in isolation. Methods using immortalized cell lines can be unreliable. HepG2 cells, a hepatic cell line, have been in culture for 20 years during which time they have ceased to be a truly accurate model of hepatic function. The use of slices of liver from dogs or rats to study bioconversion of compounds are also unsatisfactory due to variations between individual animals and broader species differences. Moreover, a number of compounds alter liver function (e.g. mibefradil, a calcium channel blocker, decreases liver metabolism, leading to the accumulation of cholesterol-lowering drugs). In a system using liver slices, one must run multiple controls on each liver slice to ensure that the data obtained are a result of the compounds being tested rather than variations in liver slices. Therefore, a highly controllable and consistent system that accurately simulates liver function would be useful in developing a better understanding of drug interactions.

A number of strategies have been developed to maintain hepatocytes in a differentiated state in culture. These strategies typically mimic components of the hepatocyte microenvironment in vivo: cell-cell interactions, cell-matrix interactions and soluble cues. For example, heterotypic cell-cell interactions play a fundamental role in liver function. The formation of this vital organ from the endodermal foregut and mesenchymal vascular structures is thought to be mediated by heterotypic interactions. Heterotypic interactions have also been implicated in adult liver physiology (i.e., localization of enzymes in zones of the liver) and pathophysiology (i.e., cirrhosis, and response to injury). In vitro, heterotypic interactions have also proved useful in stabilizing liver-specific functions in isolated hepatocytes. Hepatic cells maintain higher levels of hepatic function at when in contact with non-parenchymal cells as compared to hepatic cells (Bhatia et al, 1999). Seeding cells and maintaining them in such a manner to maintain the optimal ratio of hepatic to non-parenchymal cells is non-trivial. Thus, the maintenance of a culture of differentiated hepatocytes is non-trivial.

Three dimensional bioreactors have been developed to simulate liver function (e.g. U.S. Pat. No. 5,827,729, incorporated herein by reference). In the system, both parenchymal and non-parenchymal cells are seeded onto a porous substrate, preferably a mesh, to form a co-culture that will generate tissue in vitro. The mesh is disposed in a container having openings at both ends for media flows. The media flows contain different amounts of nutrients, waste materials, gases and other substances such that a diffusion gradient is established across the tissue. Although such a complex system allows for the growth and maintenance of hepatic cells, such a system is too cumbersome for use in high throughput screening assays.

Cell-matrix contacts are also well-defined in the adult liver, yet are disrupted in standard culture conditions. In vivo, hepatocytes are "sandwiched" by ECM in the Space of Disse. These cell-matrix contacts can be simulated by the use of a "collagen gel sandwich culture." (U.S. Pat. No. 6,133,030, incorporated herein by reference, and Dunn et al, 1992) Hepatocytes are grown on a support surface and overlaid with collagen. Hepatocytes may be maintained in a differentiated state long term in culture due to the orientation of the ECM interacting with the beta-1 integrins. However, due to the presence of the collagen cell layer as a fragile barrier to bidirectional mass transfer, this culture technique has not been amenable to scale up for clinical bioreactor applications for liver failure.

SUMMARY OF THE INVENTION

The invention is a method for the culture of cells on nanoporous silicon support for the development of bioreactors. Cells are cultured individually or in small clusters in macropores on a crystalline silicon chip that has been modified by microfabrication techniques to produce macropores of a defined size to accommodate the cell or cells of interest, either prokaryotic or eukaryotic, primary cells or cell lines. The chip is additionally modified by methods to produce nanopores in the chip to allow for the passage of media, blood, plasma, gases and other substances through the chip. Nanopores can also be used to enhance the surface area of the chip or modify the biological response of the chip due to topological effects. Nanopores may also be used to incorporate on-chip biosensors. (Victor et al, 1997, incorporated herein by reference) The macropores may be treated with collagen or other biomolecules to facilitate attachment of cells to the chip and enable pseudo-3-dimensional interaction of biomolecules with a cell surface. Thus, the cell differentiation may be maintained by a 3-dimensional cue on an essentially 2-dimensional surface. Furthermore, no transport barrier is introduced between the cell surface and the fluid stream. The invention is not limited by the method of production of the chip, but is instead concerned with the use of a nanoporous silicon chip manufactured such that the properties of the chip allow for the localization of cells in individual macrowells such that they maintain the properties of the cell type in vivo.

Chips may be seeded with single or multiple cell types. Such chips may be used to test compounds for ADMET applications, to evaluate drug interactions and biological activity, for protein or metabolite production for artificial organ support apparatuses, and for sensing of toxins in chemical or biological warfare and contamination. The bioreactor of the invention provides greater consistency than prior methods by providing a reactor that allows the insertion of a single cell into a single micropore. Thus it is possible to more rigorously control the environment of the cell.

Chips may be assembled into higher order structures for use in protein or metabolite production or in an artificial organ support apparatus. Scale-up may be achieved by vertical stacking of chips into a cartridge configuration with well-defined silicon or polymer "spacers" separating each chip. Fluids supplying nutrients and gases to the cells may flow in path through the porous chips, parallel to the chip surface, or in combinations thereof. The fluid need not be continuously flowing. However, the chips must be in constant contact with the fluid media. As the chip is essentially two dimensional and permeable, with cells exposed to the surface on both sides of the chip; therefore, it is not necessary for substances to flow through the chip to maintain the viability and function of the cells.

Lastly, the invention is the discovery that cells, specifically primary hepatocytes which are notoriously difficult to grow in culture, are viable and maintain their state of differentiation when grown on nanoporous silicon. The cells produce liver specific products including albumin and urea at levels comparable to cells grown on polystyrene, a standard tissue culture substrate. The maintenance of the desired phenotype may be enhanced by the coating of the wells with collagen or other biomolecules, inculding, but not limited to fibronectin, vitronectin, RGD and YIGSR peptides, glycosaminoglycans (GAGs), hyaluronic acid (HA), integrins, selectins and cadherins. In particular, cells are exposed to biomolecules in a pseudo-3-dimensional configuration (i.e. the walls of the well interact with the cell surface as opposed to the interactions achieved on a flat surface) mimicking the in vivo environment.

BRIEF DESCRIPTION OF THE DRAWINGS

The present invention will be better understood from the following detailed description of an exemplary embodiment of the invention, taken in conjunction with the accompanying drawings in which like reference numerals refer to like parts and in which:

FIG. 1. Schematic of a porous silicon bioreactor.

FIGS. 2A–2C. Viability and function of cells on porous silicon (A) Graph indicating the percentage of live staining cells of the total cell number as a function of time (B).

Total albumin secretion level per day over a two week period for the three conditions examined (C) Total urea production per day over a two week period for the three conditions examined.

Figure 3A:
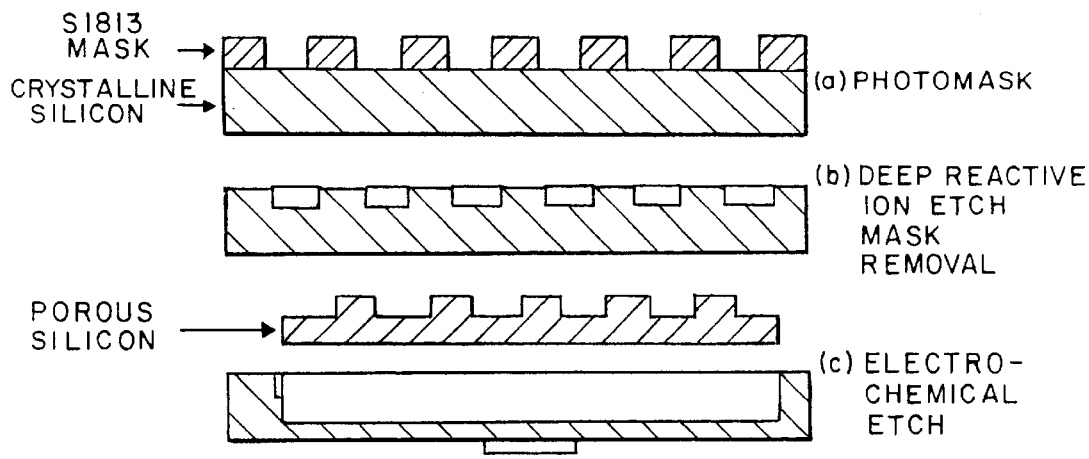
Figure 3B:
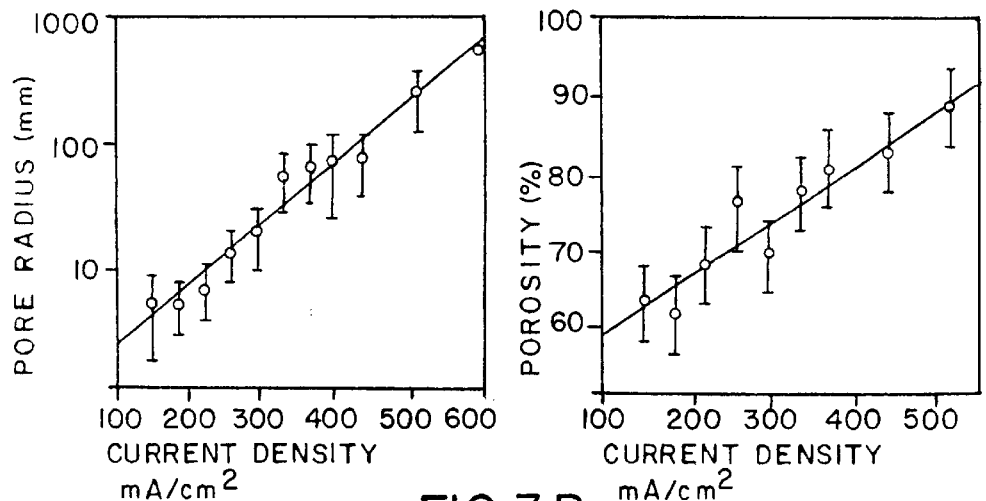
Figure 3C:
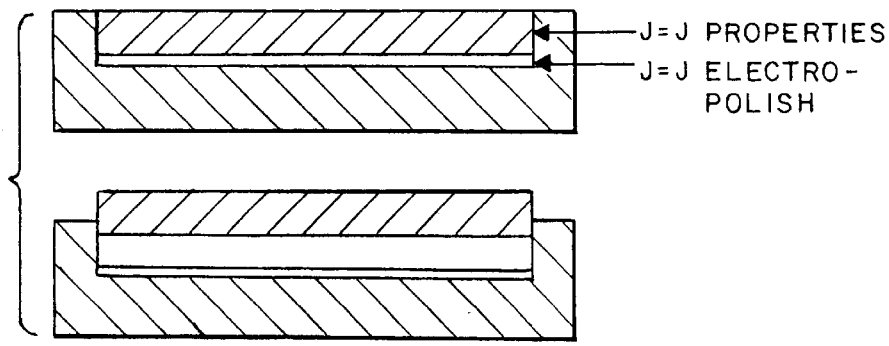

FIGS. 3A–3C. Schematic of bioreactor fabrication method using deep reactive ion etching (DRIE).

Figure 4:
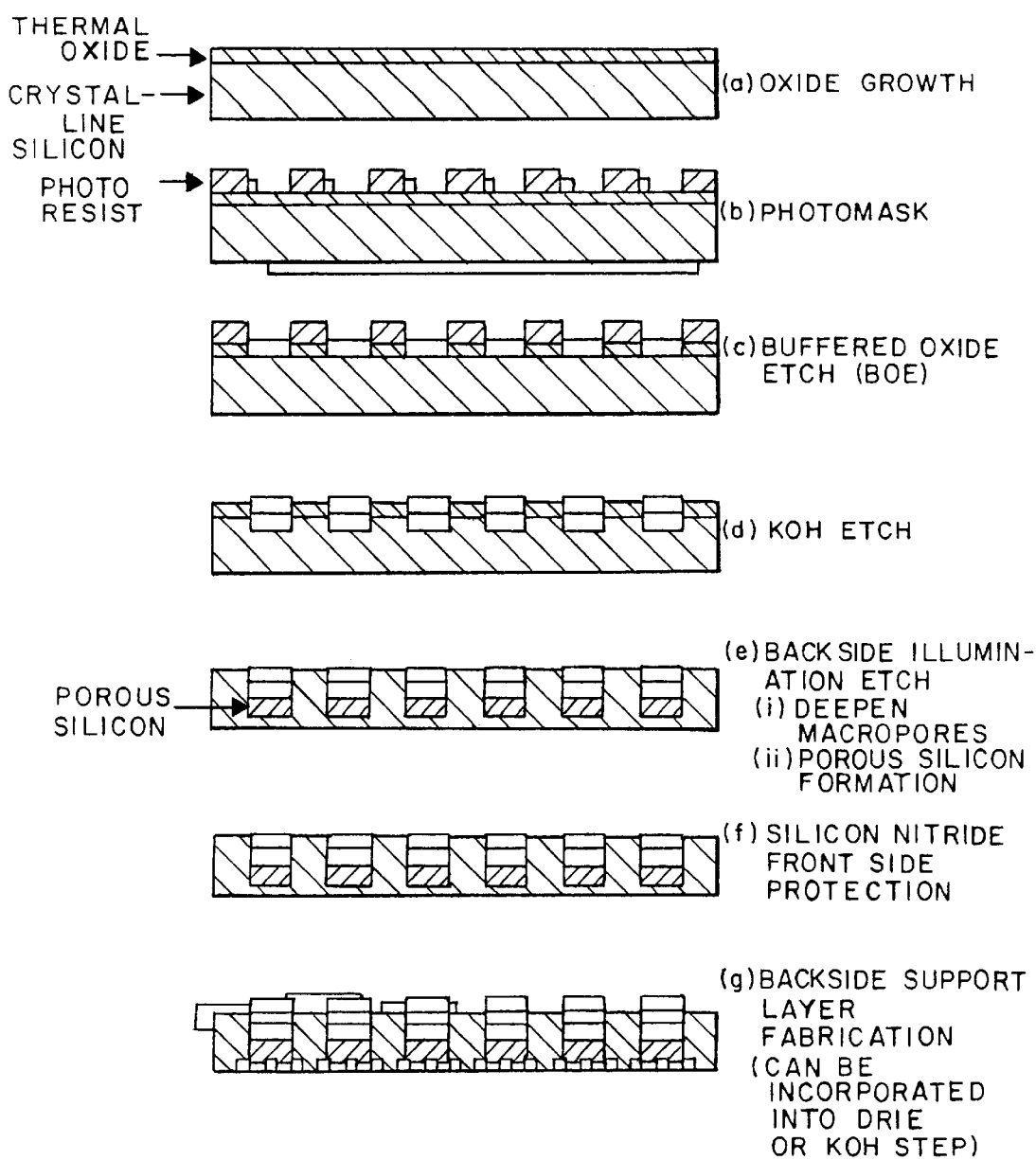

FIG. 4. Schematic of bioreactor fabrication method using wet etching techniques.

Figure 5:
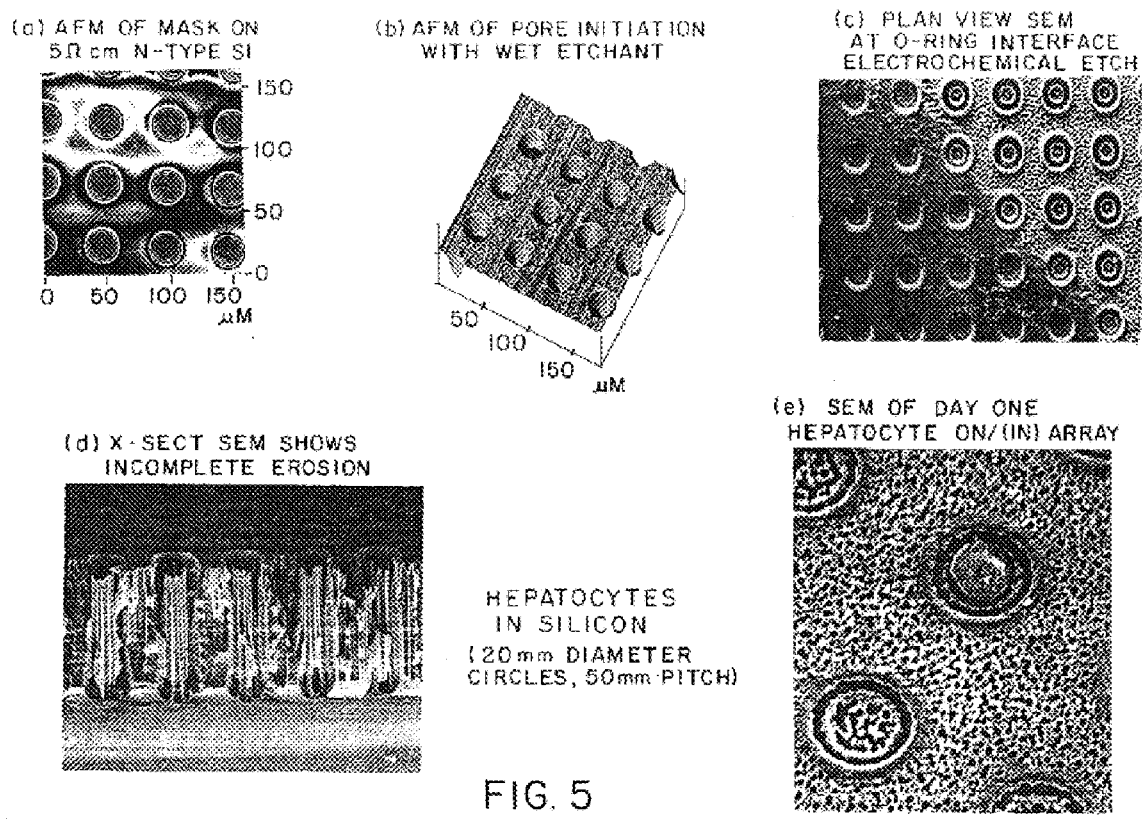

FIG. 5. (a) Atomic force microscope (AFM) image of a photorestant mask on 5 W-cm n-type silicon. (b) AFM image of pore initiation with wet etch. (c) Plan-view of a scanning electron micrograph (SEM) at O-ring interface after electrochemical etch. (d) Cross section SEM shows incomplete erosion of silicon. (e) SEM of day 1 hepatocyte in array.

DETAILED DESCRIPTION OF THE DRAWINGS

Herein we claim methods to microfabricate silicon (Si) structures to be used for culturing cells. The substrate was designed in an attempt to optimize the factors that influence a collection of cells, specifically primary hepatocytes, to mimic native organ function (Nagamori, 2000; Selden, 1999). A silicon substrate has been prepared with the aim of mimicking the supportive cytoskeleton, extracellular matrix and cell-cell contacts found in the liver in terms of structure, chemistry, and permeability. (FIG. 1) Incorporating techniques advanced in the optoelectronics industry, macropores of a diameter on the size scale of an individual hepatocytes (10–35 micron) were fabricated within a nanoporous silicon substrate. Similarly, macropores can be fabricated to correspond to the size of other cell types including β-islet cells (10–35 microns), stem cells (5–10 microns), lymphocytes (5–8 microns) or bacteria (0.5–10 microns). Macropores may also be fabricated to contain a cluster of cells (50–200 microns). Such a value will vary depending on the cell type and the number of cells to be present in the well. Current techniques allow feature sizes less than 0.2 micron to be routinely fabricated. With conventional techniques available in an average fabrication facility, less than 0.5 micron features are readily achievable. The macropores are not limited to circular shapes, but may be any of a number of shapes, especially with DRIE methods. Current methodologies allow for a range of 0.5–1000 micron wells to be readily fabricated.

The macropores provide structural support and allow intimate interaction between the cells and ECM proteins, such as collagen, attached to the oxidized silicon, whereas the nanoporous silicon material facilitates mass transfer within the cell culture. Ultimately the integration of other microfabricated (optoelectronic, chemical, and mechanical) and microfluidic networks can be envisioned incorporating multiple cell types and other active components such as sensors and actuators. Culture viability is determined by several assays monitoring the production of proteins and metabolites associated with a properly functioning liver (e.g. albumin and urea production, cytochrome P450 activity). Understanding the factors that influence healthy culture growth is a key component to ex vivo applications of cell cultures (2-dimensional and 3-dimensional) such as artificial organs or as a large-area array (2-dimensional) for studying drug-liver interactions (metabolism).

The microfabrication of silicon cellular arrays presented herein consists of three fabrication steps: patterning the crystalline silicon wafer, formation of the macropores via the dry etch method, deep reactive etch (DRIE) or a wet etch (KOH solution), and formation of the nanopores via an electrochemical etch. Both of the methods outlined below involve making the substrate porous after the macropore features have been formed in the crystalline substrate; is also possible perform a dry etch with a porous silicon substrate and form the macropores second. (See below) Once the substrate has been fabricated, it is prepared for cell culture by adsorption or covalent coupling of collagen onto ozone-oxidized Si substrates. The array of wells that contain the cells can be patterned with relative ease due to the fact that micropatterning on the super-micron size scale (size scale of individual cells) has been achieved easily for several decades in the circuit industry. Two patterns were used in our initial studies to prove the concept was possible. In the first phase of development a chrome mask for the creation of a pattern of 20 micron diameter wells separated by 50 micron center-to-center distance in a square array was used. In phase 11 development a chrome mask was constructed consisting of 15 micron diameter wells in a hexagonal array separated by 18 micron center-to-center distance. The latter array provides over 300,000 wells/cm$^2$, a seeding density that provides statistically significant cell populations in a relatively small area (assuming one cell to each well).

The attachment, viability, and function of primary rat hepatocytes, a notoriously difficult cell to grow in culture, was assayed on a number of surfaces including nanoporous silicon. Attachment and viability were assessed by fluorescent microscopy of cells probed with vital dyes on nanoporous silicon. This is in contrast to bulk metabolism assays (e.g. lactate dehydrogenase activity) that have been previously used that can be deceptively high in a system in which cells are able to proliferate. To investigate the long-term effects of the porous silicon material on cell viability and function, the maintenance of liver-specific functions over two weeks of continuous culture were examined.

The attachment and spreading of primary hepatocytes on nanoporous silicon were compared across a variety of culture conditions. The porous Si samples were prepared in an electrochemical etch as described in the Examples. The porosity of the porous Si substrates was approximately 70%, with an average pore size of 2–5 nm. The samples were then subjected to oxidizing conditions which generate a thin (approx. 5 nm) oxide layer. Initially, the cells are exposed to a silicon oxide surface rather than pure silicon; however, fourier transform infrared spectroscopy (FTIR) showed that the oxidized porous silicon also contains the Si—Si crystalline vibrational mode, indicating that nanocrystalline Si is still present. The oxidized surface is therefore similar to the surface of bioactive glass, which has been shown to be compatible with osteoblasts. Although this renders the silicon surface less electroactive, electrical control of the surface may be retained through electron tunneling through the thin oxide layer.

Primary hepatocytes were seeded onto various porous Si substrates in the absence of adhesive serum proteins, in 10%-serum containing media, and in the presence of both 10%-serum containing media and collagen I coating. After 24 hours, cells were labeled with fluorescein diacetate and observed for viability, attachment and cell spreading. Images were recorded using a Nikon Diaphot microscope equipped with a SPOT digital camera (SPOT Diagnostic Equipment, Software version 2.2, Sterling Heights, Mich.), and MetaMorph Image Analysis System (Universal Imaging, Westchester, PA.) for digital image acquisition. Viability of the cells was determined using the vital dyes fluoroscein diacetate (FDA, Sigma) and propidium iodide (PI, Sigma). Immediately prior to imaging, cells were labeled with 2 ml of a solution containing 5 μg/ml PI and 5 ng/ml FDA. Hepatocytes on silicon were inverted onto supports prior to labeling to facilitate microscopy. The labeled hepatocytes were immediately viewed by fluorescence microscopy using excitation wavelength settings of:492/517 and 541/565 nm for FDA and PI respectively. Viability was then quantified using the MetaMorph Image Analysis system with 10–15 fields per condition per day.

Cells appeared to preferentially adhere and spread on porous silicon in the presence of type I collagen. In the absence of collagen but in the presence of serum and associated adhesion molecules (e.g. vitronectin, fibronectin, etc.), some cells attach and spread well, but to a lesser degree than the collagen adsorbed case. In the absence of any non-endogenous cell adhesion molecules, cell attachment was sparse and spreading was minimal. The percent of surface area covered by cells was determined by image analysis. There was significantly more coverage on the collagen treated porous silicon ($32\pm3.6\%$) than on either the serum treated or untreated porous silicon ($19\pm3$ and $6\pm0.7\%$ respectively). The serum-treated sample also displayed significantly more cellular coverage than the untreated sample.

Variations in cell attachment was due to the difference in the chemical, rather than the physical state of the silicon substrate. Using nanoporous silicon, the physical and chemical properties of a substrate may be decoupled in this system. Through atomic force microscopy (AFM) imaging, the topology of the substrate surface was characterized and shown to be similar irrespective of the chemical modification used. AFM was performed on chemically modified surfaces using methods identical to those used in cell culture to demonstrate the presence of attached collagen and to detect other variations that may have been induced in the process of the chip preparation. AFM images were obtained under ambient conditions using an Nanoscope IIIa multimode scanning probe microscope (Digital Instruments, Santa Barbara, Calif.) operating in a TappingMode using a 4–10 nm nominal radius (IBM supercone probe) tip. Roughness measurements were determined as area statistical root mean squared (rms) roughness, the standard derivation of the z-data, using an algorithm provided in the instrument software. AFM revealed that the nanotopology of the porous silicon is relatively unchanged with the addition of cell matrix and adhesion molecules, implicating surface chemistry as the dominant variable. The similarity of the images suggests that differences in cell attachment were the result primarily of the chemical modification rather than the nanotopology of the surface.

The long-term effects of continuous hepatocyte culture in the presence of porous silicon as compared to crystalline silicon and tissue culture polystyrene are presented in FIG. 2. FIG. 2A shows the percent of adherent cells that are viable on porous silicon for the first 5 days after isolation. Cells in all conditions remained viable at comparable levels, suggesting that cell viability on nanoporous silicon approached that found on a comparative biocompatible standard, tissue culture polystyrene.

FIGS. 2B and 2C indicate rates of albumin and urea production of the cultures over two weeks. The synthesis of albumin is a widely accepted marker of hepatocyte synthetic function, and the secretion of urea is an indicator of an intact nitrogen metabolism pathway. The daily production of both albumin and urea in the porous silicon cultures are comparable to cells cultured on polystyrene as well as crystalline silicon over the entire culture period. These data suggest that there are no gross, long-term (on the order of weeks) cytotoxic effects of nanoporous silicon on primary hepatocytes despite the harsh electrochemical reaction conditions and high concentrations of hydrofluoric acid (HF) used in the preparation of porous Si. The production of silane from porous silicon degrading in an isotonic solution, observed in Canham et al (1995), also does not seem to affect hepatocyte function.

Primary hepatocyte cultures are notoriously difficult to maintain in a differentiated state. The demonstrated viability and maintenance of liver function observed in this system indicate that it would be useful for the maintenance of other cell types that are less problematic to maintain in culture. For example, β-islet cells could be maintained for the production of insulin. By modulating the size of the macropore, cells with unknown adhesive properties, such as stem cells that tend to be smaller than parenchymal cells, could be isolated for growth.

Cells transfected with a library of DNA constructs can be isolated and observed individually in macropores. For example, a single cell type containing a reporter gene (e.g. green fluorescent protein) whose activity is regulated by hormone levels, can be transfected with a library containing genes encoding randomly mutated hormone receptors. Transfected cells can be seeded into the chip which can then be treated with hormone. Cells containing a functional hormone receptor can be easily visualized as green cells. Due to the nature of the invention, cells are already isolated and single cells of interest can be recovered for PCR analysis using a micropipette or other micromanipulation tools such as optical tweezers. Similarly, cells can be transfected with a reporter construct that randomly integrates into the genome. The regulation of the upstream promoter can by monitored by the production of the reporter construct. Thus, environmental stimuli that produce changes in promoter activity (e.g. soluble factors, cell-cell interactions, cell-matrix interactions) or phenotypic changes that cause changes in promoter activity (e.g. differentiation of a stem cell) can be monitored. Cells would not be subjected to the relatively hostile sorting procedures such as flow cytometery or micropipetting. In addition, the localization of cells for subsequent experimentation is accomplished by spatial addressing (i.e. position in the array). A similar assay performed in a multiwell plate would require cells be sorted into individual wells as one would not be able to easily isolate a single cell from a mixed tissue culture dish thereby requiring larger volumes of candidate compounds. Thus the method offers an improvement over current practice in terms of time and effort required.

The chip of the system can also be used as a scaffold for cells to be subjected to a gene transfer protocol. A mixture of cell types can be seeded into a single scaffold. The cells are then infected with a virus or subjected to another gene transfer protocol to insert a reporter gene (e.g. GFP) into the cells. Cells can be observed to determine what types of cells have taken up the reporter gene. This may be done by direct observation of the cell to identify the cell type. Cell type can be ascertained by staining for specific cell type markers. Using image processing software already developed for DNA microarray technologies, identification of affected cells is rapid and automated.

Non-adherent cells can be cultured in the chip of the present invention by passing growth media through the chip such that the cells would be retained in the macropores. For example, lymphocytes, either a homogeneous population producing a single antibody or a mixed population producing a mixed population of antibodies, could be maintained in such an apparatus. The nanopores would allow the passage of the media through the chip. Using the apparatus of Griffith, cells would be forced through the chip along with the media. Non-adherent cells cannot be grown in any of the other microarray systems previously described.

The range of macropore sizes possible in the chip of the application can be reduced to provide a scaffold for the growth of prokaryotic cells (macropore size 0.5–10 microns) to provide a microarray for a number of assays. For example, bacteria such as *E. coli*, can be readily transformed with a library of plasmids containing a reporter gene (e.g. GFP) with a variety of putative transcription promoter regions ahead of the reporter gene. Bacteria are seeded into macropores. Chips are exposed to putative transcriptional activating factors. Bacteria expressing GFP can be easily identified, removed from the chip by a micromanipulator and subjected to a PCR reaction to determine the promoter from which transcription was activated. A similar assay could be envisioned using eukaryotic cells transfected with a library of similar constructs.

Macropore sizes may also be increased for the growth of clusters of eukaryotic cells. Cell-cell contacts have been shown to be helpful, although not necessary, in the maintenance of hepatic and other parenchymal cell types. Understanding the interaction between cells and the processes of cell-cell communication can be facilitated by the use of the instant invention.

In summary, porous silicon is a nanoporous semiconductor substrate that couples many of the beneficial features of crystalline silicon with unique properties such as its capability to act as a biosensor and the tunability of pore sizes over biologically relevant length scales. Hepatocytes are capable of attachment to both nanotextured (2–1000 nm) and microtextured (1–100 micron) surfaces, but show some preference for a nanotextured surface. Both a long-term biochemical study and direct fluorescent imaging of live cells have demonstated that primary cells attach, spread, and function on this material.

These results demonstrate the feasibility of integrating existing porous silicon biosensor technology with functional cells, which may enable real-time, non-invasive monitoring of cellular function and metabolism and aid in the formation of complex BioMEMS (Biological Micro-Electro-Mechanical Systems). Researchers have been able to monitor cellular metabolism using electrical impedance, the generation of protons, fluorescence assays and action potentials in excitable cells (Kapur et al, 1999). Furthermore, tuning of pore size provides a tool to examine the effects of nano- to micro-scale topography on cell behavior independent of surface chemistry (Curtis et al, 2001; Curtis et al, 1997; Webster et al. 2000).

The bioreactors of the instant invention can be used in a system such as that described by Griffith (U.S. Pat. No. 6,197,575 incorporated herein by reference) in a manner analogous to the microtissue arrays described in that patent. The system can be used to screen materials for biological activity, to test the effect of the cells on the materials (metabolism), to test a material on a biological that must first infect cells or tissues, such as viruses, or to provide an environment for gene therapy. Such assays can be set up in a high throughput screening method for the identification of active drugs, or in a low throughput setting to test for the presence of pathogens in a bodily fluid taken from a subject. Such a system can be used to model organ function in any of a variety of assays.

The bioreactor of the invention can be used in the context of a hepatic support apparatus. A number of such extracorporeal liver devices have been described, such as those by Naughton et al. (U.S. Pat. Nos. 5,827,729 and 6,218,182; also Allen et al, 2001, all incorporated herein by reference). A number of individual bioreactor chips of the instant invention can be assembled into a complex of bioreactors as described above to provide sufficient capacity for the volume of blood to be processed. Blood or plasma is perfused through the assembly of chips for the detoxification of blood and to provide liver specific enzymes and proteins to the individual on the hepatic support appartus.

EXAMPLE 1

Materials. All silicon substrates used in this application were purchased as <100>-oriented, one-side polished, 4" wafers. Highly conductive p-type (r<1 mW·cm) were purchased from Siltronix. Standard p-type (r=1–5 W·cm) and n-type (r=1–5 W·cm) (r=1–3.5 kW·cm) were purchased from Silicon Quest International. Hydrofluoric acid solutions [HF(aq)] were obtained as 49% aqueous solutions and diluted with ethanol (EtOH) to the desired concentration. Suface oxides were grown using a Lindberg/Blue ceramic oven. Photopatterning was perfomed using S1813 positive resist (Shipley), an Headway Research spinner, and an HTG contact mask aligner. Chrome masks were made to order by Photoscience Inc. Deep Reactive Ion Etching (DRIE) was performed using PlasmaTherm SLR 770 ICP DRIE machine. Electrochemical etching was performed in a homeade Teflon® etch cell using an aluminum back contact on the silicon and a platinum counter electrode in solution.

EXAMPLE 2

Photolithography. Silicon wafers were cleaned before application of the positive photoresist. Silicon wafers were cleaned in HCl:MeOH (1:1) and rinsed in deionized water before application of the positive photoresist (Cras et al, 1999). Alternatively, sequential sonication for 5 min. in acetone, isopropanol, and DI water nay be done. The silicon substrates were dried in a 90° C. oven for 90 sec. An approximate 1 micron thick coating of S1813 photoresist was spun onto wafers at 4000 r.p.m. for 25 seconds. The coated chips were then soft baked in a 90° C. oven for 3 min. Masking was performed using a chrome mask and exposing the wafers to UV light of an intensity ~2 mW/cm$^2$ for 35 sec. The wafer was then placed in 90° C. oven for 6 min. after which it was developed in MF319 developer for 90 sec. The patterned substrate was then placed in a 110° C. oven for 30 min. in order to harden the mask (post-bake). Additionally other etching techniques may be used to stabilize the chips. These techniques include the use of a protective silicon nitride mask on the porous structure and micromachining a supportive framework of large feature size on the backside of the chip.

EXAMPLE 3

Methods of Fabricating Silicon Microstructures. Macropores of sizes ranging from 0.5–100 microns may be fabricated using the following three approaches. Methods 1–2 require that further processing as described in Example 4 to created the porous silicon membrane, but in Method 3, the entire chip may be processed in a single step.

1. Deep Reactive Ion Etch (DRIE) The deep reactive ion etching (DRIE) process is a gas phase technique (dry etch) in which successive passivating/etch steps are performed by exposure to $C_4F_8$ and $SiF_6$, respectively. Using the DRIE process, highly anisotropic etches may be created in silicon. A sacrificial oxide layer is not required for this process, unlike the more common wet etch techniques (discussed below). Resist is removed in the DRIE process, however the rate of removal is slow relative to the rate of silicon removal, and thus provided sufficient protection so that the macropores can be produced efficiently. Advantages of the DRIE method include the very high aspect ratio structures generated, the high degree of precision, and the ease of sample preparation. We have also investigated other methods including wet etches with KOH solutions and electrochemical etching of low-doped n-type silicon with backside illumination. (See below) A drawback to the latter methods is that an additional step is needed for a protective layer such as silicon nitride or silicon oxide and additional etch steps to form the initial macropores. The macropore shape is also less easily defined using the KOH wet etch as the etch is highly crystal-orientation dependent. The major advantage to using the wet etch methods is in the low cost of materials and equipment, however the DRIE processing is the most efficient.

2. Wet Etching Another method of forming micron-sized features is the use of KOH solutions (Kendall, 1979; Williams, 1999). This etching solution is orientation dependent; etch rates for various crystal faces are approximately 600:300:1=<110>:<100>:<111> (Williams and Muller, 1996) Thus, the use of <100>-oriented wafers implies that etching will result in inverted square-pyramidal facets with metric openings predetermined by the mask. As photoresist is quickly dissolved in alkaline solutions, a silicon oxide or nitride mask is required. The formation of facets in <100> silicon has been successfully performed using the following approach. An oxide layer is formed by heating the wafers in a stream of oxygen at 1100° C. The thickness of the oxide is determined by the time of exposure (Kendall, 1979; Williams, 1999). Since silicon oxide is slightly soluble in the KOH solutions a thickness greater than 60 nm is desired for formation of (15 microns)$^2$ facets. The wafers are then patterned with S1813 positive resist as outlined above. The exposed oxide is then removed by exposure to buffered oxide etch (BOE) which is composed of 5 parts (by weight) 40% aqueous ammonium fluoride ($NH_4F$) solution to 1 part aqueous HF (49%) (Williams and Muller, 1996). The photoresist is then removed and the wafers are immersed in stirred solution of 80° C. KOH solution. The recipes for the KOH solution vary throughout the literature and etch rates can be vary depending on ratios. Typically we have used solutions composed of (by weight) the following 1:4= KQH:$H_2O$ and some authors have reported good results with 2:1 ratio.

3. Photoelectrochemical Etching If low-doped n-type silicon is used, a backside illumination etch can be incorporated to etch the macropores. The depth of the wells can be controlled with the proper each conditions (Kleinmann, et al, 2000; Lehmann et al, 1993; Lehmann et al, 1990; Muller et al, 2000). A current is chosen based on a ratio of the area of the macropores: total area is multiplied by the electropolishing current density for a given HF concentration. Holes ($h^+$) are generated by shining light on the backside of the wafer (opposite to the solution/Si interface). The holes migrate towards the solution interface due to the applied bias but tend to concentrate at the pore bottoms due to the bending of the electrical field lines at the solution/Si interface due to the pattern of initial etch pits in the silicon wafer. By controlling the light intensity and the applied voltage, the current and subsequently the rate of silicon dissolution can be controlled so that etching only occurs at the bottom of the macropores. If the etch conditions are not optimized incomplete dissolution can occur and the substrate can be made porous throughout (FIG. 5d). By varying the potential, current density, HF concentration and silicon dopant density, lift-off patterned porous Si membranes can be achieved.

EXAMPLE 4

Electrochemical Etch. Once the macropores have been formed in the silicon substrate a two-step electrochemical etch in ethanolic HF is performed. There exist numerous variables in the formation of porous silicon however several primary factors have been identified to control pore size and porosity: the type and density of dopant atoms, HF concentration, and current density (J). The methodology that most easily achieves a wide range of variability incorporates highly B-doped silicon ($p^{++}$-type; r<1 mW·cm ). One disadvantage of using $p^{++}$-type silicon is that the photoconductive effect is much less pronounced than lower doped Si wafers. More exotic applications of the silicon bioreactors are possible with lower doped Si .(Sailor and Lee, 1997)

In the first step, etching is performed at a current density that provides the desired porosity and pore size. The thickness of the layer is chosen considering the duration of the etch (FIG. 3). In the second lift-off step a current density is chosen near the electropolishing condition facilitating the removal of the patterned porous substrate. A typical lift-off step involves etching at J=50 mA/cm$^2$ in 3.3 wt % HF solution for 30 sec. A critical factor in developing these patterned arrays is the fact that the porous structures are very fragile and many times crack during drying due to the surface tension of the evaporating solvent. Two approaches critical point drying (Bellet and Canham, 1998) and "all-wet" processing have been used thus far to alleviate this problem.

The approaches to stabilizing highly porous structures include critical point drying in $CO_2$. The "all-wet" methodology avoids a drying step by maintaining higher surface tension conditions due to evaporating solvent. During drying, the porous framework is subject to large mechanical stresses due to surface tension existing between porous material and the evaporating solvent. These stresses may cause the porous silicon substrate to tear, curl or collapse. Critical point $CO_2$ has virtually non-existent surface tension. In the "all-wet" methodology, all manipulations of the chip are performed without subsequent drying steps. For example, after the formation of a lift-off patterned membrane, with top and bottom referenced, the substrate is rinsed in three successive solutions of ethanol to remove the HF used in the electrochemical etch. The membrane can be oxidized using a chemical reagent such as pyrimidine or other weak base, or ozone oxidized via a bubbler in an ethanol bath. After rinsing in ethanol, the oxidized substrate is rinsed three times in culture medium, optionally subjected to treatment with cell adhesive reagents and seeded with cells. Thus, the porous substrate is never subjected to surface tension forces associated with drying.

EXAMPLE 5

Hepatocyte Isolation and Culture. Hepatocytes were isolated from 2–3 month old adult female Lewis rats (Charles River Laboratories, Wilmington, Mass.) weighing 180–200 g, by a modified procedure of Seglen. Detailed procedures for isolation and purification of hepatocytes were previously described by Dunn et al (1991). Briefly, 200–300 million cells were isolated with viability between 85% and 95%, as judged by trypan blue exclusion. Nonparenchymal cells, as judged by their size (<10 micron in diameter) and morphology (nonpolygonal or stellate), were less than 1%. Culture medium was Dulbecco's modified eagle medium (DMEM, Gibco) supplemented with 10% fetal bovine serum (FBS, Sigma, St. Louis, Mo.), 0.5 U/mL insulin, 7 ng/ml glucogon, 20 ng/ml epidermal growth factor, 7.5 µg/ml hydrocortisone, 200 µg/mL penicillin, and 200 µg/ml streptomycin.

EXAMPLE 6

Collagen Adsorption and Cell Seeding. Once the substrates have been formed the next task is to prepare the substrates for cell seeding. Collagen adsorbs readily to the oxidized silicon substrate as the silicon oxide surface is negatively charged even at moderately low pH values. Collagen is positively charge at physiologic pH due to the abundance of lysine resides and the amino ($-NH_2$) side chains. Alternatively, collagen or other ECM components may be covalently attached to the surface of the chip through any number of bioconjugate techniques. On chips etched by DRIE with residual photoresist, collagen adsorption can be performed followed by a lift-off step in acetone, producing selective coating of the macropores to promote increased selectivity in cell adhesion.

Seeding the cells is accomplished by exposure of the substrate to a high density "solution" of cells usually by pouring the cells onto the substrate. Entry of cells into wells is dependent upon having a sufficiently high density of wells such that the cells do not attach to the area surrounding the wells, and having sufficiently large wells. For seeding of individual hepatocytes or β-islet cells into macropores, macropores should range in size from 15–25 microns across with less than 15 microns between macropores to prevent the cells from adhering to the surface of the chip rather than entering the macropore. For prokaryotes, macropores would range between 0.5 and 10 microns with less than one micron in between wells. Stem cells and lymphocytes would be seeded onto a chip with wells and spaces intermediate to the two examples above. Individual cells attached in individual wells have been observed by cross-sectional SEM. The invention is not limited by the method used to seed the cells into the wells.

EXAMPLE 7

Cell Culture on Crystalline and Porous Silicon Hepatocytes were cultured on silicon chips prepared in the following manner: Porous Si samples were prepared by anodically etching p-type silicon (5–10 W/cm resistivity, (100) orientation, B-doped, supplied by Silicon Quest Inc.) in a 1:1 v/v mixture of ethanol and aqueous hydrofluoric acid (49%) at 5 mA/cm$^2$ for two minutes in the absence of light. A mesh Pt counter electrode was used to ensure a homogenous electric field. Each sample was then rinsed thoroughly with ethanol and dried under a nitrogen stream.

Crystalline Si samples were rinsed with ethanol and dried under nitrogen stream. Both types of Si samples were exposed to ozone for 15 minutes using an ozone generator (Ozomax, Quebec, Canada) with a flow rate of 8 g/h of $O_3$ to provide a stable, oxidized, silanol-terminated surface.

Prior to cell seeding, Si samples were cleaned by exposure to oxygen plasma on a Technics 500 II Asher at a base vacuum of 80 mTorr and $O_2$ pressure of 120 mTorr at a power of 100 W for 4 minutes. Samples were then sterilized by immersion in 70% ethanol for 1 h. After sterilization, samples were rinsed 4 times in sterile water. Collagen I was adsorbed to the surface by incubation with 0.25 mg/mL collagen I (Vitrogen, Cohesion Technologies, Palo Alto, Calif.) for 1.5 h at 37° C. As a control, collagen I was also adsorbed to polystyrene cell culture wells (Falcon). After incubation, Si samples were washed with sterile water and placed in the cell culture well pre-treated with 0.1% bovine serum albumin (BSA) to prevent cell adhesion on non-Si surfaces. Hepatocytes were seeded in culture media and allowed to attach overnight.

EXAMPLE 8

Functional Analysis of Hepatocytes on Silicon Substrates. After overnight attachment, the samples were washed once with media. The substrates were overlaid with a layer of collagen gel to stabilize cell function (Dunn et al, 1989).

Specifically, a 10:1 Vitrogen: 10×DMEM solution was applied and allowed to gel for 1 h at 37° C. After gelation, culture media was added. Media was collected and changed every other day for twelve days. Samples were stored at −80° C. for subsequent analysis for urea and albumin content. Urea synthesis was assayed using a commercially available kit (Sigma Chemical Co., kit No. 535-A) Albumin content was measured by enzyme-linked immunosorbent assays (ELISA) as described previously (Bhatia et al, 1999). Rat albumin and anti-rat albumin antibodies were purchased from ICN/Cappel Laboratories (Cochranville, Pa., USA).

EXAMPLE 9

Assembly of Multiple Individual Chips for Increased Capacity. There are several methods the original module may be scaled up to simulate physiological levels of organ function. Once seeded, the chips are stacked directly on top of each other to so that the cells are sealed by porous silicon from the top and bottom. This embodiment of the reactor would function much like a packed bed plug flow reactor. In another embodiment, the chips are again stacked, but they are separated and have openings on the ends, much like a plate tower distillation column. This would lessen the pressure required to achieve the desired flow rate through the reactor. Assembly may also be done in a parallel plate format, where the flow is directly horizontally over the chips and some media is allowed to flow through the porous silicon.

For example, if there are 300,000 hepatocytes/cm$^2$ on a chip of 6 inch diameter functioning at in vivo levels, then approximately 130 chips are needed to achieve a minimum level of physiological function for a human. Large scale reactors are preferred for use in hepatic support or protein and metabolite production.

EXAMPLE 10

Screen for Biological Activity of Bioactive Compounds. A homogeneous or heterogeneous cell population is seeded into the a silicon chip of the instant invention. Cells are allowed to attach. A compound of interest, a putative drug, toxin or other bioactive compound, is added to the growth media of the bioreactor. Alternatively, a mixture of compounds can be added to the bioreactor to test drug interactions. A manual high throughput assay can be envisioned by placing individual chips into individual wells in a multiwell plate. Alternatively, it may be done using an automated system such as that described by Griffith (U.S. Pat. No. 6,197,575). Cells are monitored under physiological conditions for response to the compounds tested by bioassay performed on the perfused fluid or by direct observation of the cells in the bioreactor. Cells can be monitored for signs of toxicity (e.g. change in metabolism or viability) or responses characteristic of prototypic toxins (e.g. apoptosis, upregulation of key pathways such as cytochrome P450 enzymes by activation of the SRX nuclear receptor). The activity of the compound may be detected in situ using an intra- or pericellular probe.

Compounds may be recovered from the growth media and assayed to determine if and how the compound was metabolized by the cell. The products of metabolism can reveal what enzymes were responsible for the processing of the compound. Thus it may be categorized into a class of molecules. Such information is useful in predicting drug interactions by determining if compounds are processed by the same mechanism.

EXAMPLE 11

Protein Production or Biotransformation. Bioreactors containing the cells of interest are assembled into a large scale reactor using the method of Example 11. Cells may express an endogenous protein (e.g. antibodies from lymphocytes; insulin from β-islet cells) or they may be used to express heterologous proteins from nucleic acids transferred into the cell by any of a number of methods. Such a system is useful for the production of secreted proteins. Cells are seeded into wells and allowed to attach. If required, factors are added or removed from the culture media to induce the production of protein (e.g. removal of tetracycline to de-repress a tetracycline promoter). Cells may be continuously perfused using a recirculating pump that pumps media through the chamber in which the bioreactors are held. The orientation of the perfusion may be essentially any orientation if the cells are adherent. If the cells are non-adherent (e.g. lymphocytes) the bioreactors are perfused with media flowing in a direction perpendicular to the bioreactors to retain the cells in the macropores. The cells may be continuously perfused with fresh media or be maintained without perfusion in the case of attached cells. After protein expression, media is collected and proteins of interest are purified by any of a number of methods well known to those skilled in the art. As the cells are viable and maintain their state of differentiation in the bioreactor of the invention, the media may be changed upon depletion of nutrients for continuous protein production.

Biotransformation of compounds can be performed in a similar reactor. The compound is added to the growth media of the cells. After the allotted time, the media is collected and the compound is analyzed by HPLC or other methods well known to those skilled in the art.

EXAMPLE 12

Isolation and Study of Stem Cells. One of the difficulties of studying stem cells is the lack of known markers to allow for cell sorting. As a result, it is possible to obtain an enriched population, but it is difficult to isolate a population of pure stem cells. Using the instant invention, one can isolate stem cells by size as they are known to be smaller than their differentiated daughter cells. Differentiation and growth factors can be added to the stem cells in culture to determine their effects on growth, differentiation and the induction of various markers. Moreover, the method could be used to study cell-cell and cell-matrix interactions in stem cells.

References

Allen, J. W. et al., Hepatology, 2001. 34:447–55.
Bellet, D. and L. T. Canham, Advanced Materials, 1998. 10:487–90.
Bhatia, S. N. et al., Advances in Heat and Mass Transfer in Biotechnology, 1997. 37:99–103.
Bhatia, S. N. et al. FASEB J., 1999. 13:1883–1900.
Canham, L. T., Adv. Mater., 1995. 7:1033–1037.
Canham, L. T. et al., Advances in Microcrystalline and Nanocrystalline Semiconductors, Boston, Mass., 1997. pp. 579–90.
Canham, L. T., et al., Adv. Mater., 2000. 11:1505–1507.
Chen, C. C. et al., Science, 1997, 276:398–401.
Cras, J. J., et al., Biosensors & Bioelectronics, 1999. 14:683–688.
Curtis, A. and C. Wilkinson, Biomaterials, 1997. 18:1573–1583.
Curtis A. and C. Wilkinson, Trends Biotechnol., 2001. 19:97–101.
Dunn, J. C. et al. FASEB J., 1989. 3:174–177.
Dunn, J. C. et al. Biotechnol Prog 1991. 7: 237–245.

Dunn, J. Y. C. et al., J Cell Bio., 1992. 116:1043–1053.
Hodgson, J. Nat. Biotech., 2001. 19:722–726.
Kapur, R., et al., Biomed. Microdevices, 2:99–109.
Kendall, D. L., Ann. Rev. Mater. Sci., 1979. 9:973–403.
Kleimann, P. et al. Materials Science and Engineering B, 2000. 69–70(29-33).
Lehmann, V. and H. Foil, Journal of the Electrochemical Society, 1990. 137:653–659.
Lehmann, V., Journal of the Electrochemical Society, 1993. 140:2836–2843.
Mayne, A. H., et al., Phys. Stat. Sol. (a), 2000. 182:505–513.
Meyer, J. -U. and M. Biehl, J. Micromech. Microeng., 1995. 5:172–174.
Muller, F., et al., Phys. Stat. Sol., 2000. 182:585–590.
Nagamori, S., et al., Journal of Gastroenterology, 2000. 35:493–503.
Rosengren, A et al., *Phys Status Solid a-Appl Res,* 2000, 182:527–531.
Sailor, M. J. and E. J. Lee, Advanced Materials, 1997. 9: p. 783–793.
Selden, C. et al. Gut, 1999. 44:443–446.
Steiner, P. and W. Lang, Thin Solid Films, 1995. 255:52–58.
Stewart, M. P. and J. M. Buriak, Advanced Materials, 2000. 12:899–869.
Thomas C. H., et al., J. Biomechanical Engineering, 1999. 121:40–48.
Victor S. -Y. et al. Science, 1997. 278: 840–843.
Webster, T. J. et al. Biomaterials 2000, 21:1803–1810.
Williams, K. R. and R. S. Muller, Journal of Microelectromechanical Systems, 1996. 5:256–269.
Williams, K. R., *Etching, in Properties of Crystalline Silicon,* R. Hull, Editor. 1999, INSPEC. pp. 809–824.

Although an exemplary embodiment of the invention has been described above by way of example only, it will be understood by those skilled in the field that modifications may be made to the disclosed embodiment without departing from the scope of the invention, which is defined by the appended claims.

We claim:

1. An apparatus comprising
a nanoporous silicon support comprising a plurality of macropores which support the viability of cells and
at least one individual cell within one of said plurality of macropores,
wherein nanopores of the support allow the at least one individual cell to obtain nutrients from a culture medium and oxygen sufficient to maintain the viability of the at least one individual cell, and the nanopores do not allow the at least one individual cell to pass through the support.

2. The apparatus of claim 1, wherein the macropores have a diameter between 0.2 and 200 microns.

3. The apparatus of claim 1, wherein the macropores have a diameter between 0.2 and 150 microns.

4. The apparatus of claim 1, wherein the macropores have a diameter between 15 and 25 microns.

5. The apparatus of claim 1, wherein the cells are eukaryotic cells.

6. The apparatus of claim 1, wherein the cells are hepatic cells.

7. The apparatus of claim 1, wherein the cells are prokaryotic cells.

8. The apparatus of claim 1, wherein the macropores are coated with a coating substance selected from the group consisting of biomolecules, peptides and proteins that wherein said proteins promote cell adhesion on biocompatible polymers.

9. The apparatus of claim 8, wherein the coating substance is selected from the group consisting of collagen, fibronectin, vitronectin, RGD and YIGSR peptides, glycosaminoglycans (GAGs), hyaluronic acid (HA), integrins, selectins and cadherins.

10. The apparatus of claim 1, wherein the support is prepared using a method selected from the group consisting of micromolding, electrodeposition machining, laser ablation, laser drilling, micromaching, wet etching, reactive ion etching, lithographic galvanic fabrication (LIGA) and embossing.

11. An apparatus comprising a plurality of nanoporous silicon supports containing cells in a single apparatus to increase throughput of the single apparatus
wherein each of the plurality of nanoporous silicon supports comprise a plurality of macropores which support the viability of cells and at least one individual cell within one of said plurality of macropores,
wherein nanopores of the support allow the at least one individual cell to obtain nutrients from a culture medium and oxygen sufficient to maintain the viability of the at least one individual cell, and the nanopores do not allow the at least one individual cell to pass through the support.

* * * * *